United States Patent [19]

Sebille et al.

[11] Patent Number: 4,696,937
[45] Date of Patent: Sep. 29, 1987

[54] THIOSULFONATE DERIVATIVES FOR INHIBITING MALFORMATION OR DESTRUCTION OF RED BLOOD CORPUSCULES

[75] Inventors: Bernard Sebille, Clamart; Yves Beuzard, Paris; Henri Demarne, Montpellier, all of France

[73] Assignees: Sanofi; Institut National de la Sante et de la Recherche Medicale (Inserm), both of Paris, France

[21] Appl. No.: 797,521

[22] Filed: Nov. 13, 1985

[30] Foreign Application Priority Data

Nov. 13, 1984 [FR] France .................. 84 17286

[51] Int. Cl.⁴ .................. A61K 31/47; A61K 31/415; C07D 401/12; C07D 233/84
[52] U.S. Cl. .................. 514/314; 514/312; 514/363; 514/369; 514/398; 546/157; 546/172; 548/141; 548/186; 548/337
[58] Field of Search .................. 548/337; 546/172; 514/314, 398

[56] References Cited

U.S. PATENT DOCUMENTS 4,324,793 4/1982 Hagen et al. .................. 548/337

OTHER PUBLICATIONS

Chemical Abstracts, 96:113510s, (1982) [Jpn. Kokai 81, 99,335, 8/10/81].
Chemical Abstracts, 99:222446h, (1983) [Jpn. Kokai 57, 147,627, 9/11/82].

Primary Examiner—Richard A. Schwartz
Attorney, Agent, or Firm—Bacon & Thomas

[57] ABSTRACT

The invention relates to novel thiosulfonate derivatives of general formula:

$$R-S-SO_2-R_1$$

in which R represents a 1H-imidazol-2-yl, quinolin-2-yl, 5-amino-1,3,4-thiadizol-2-yl or 4,5-dihydro-thiazol-2-yl radical and $R_1$ represents a lower alkyl, (hydroxy)lower alkyl, phenyl, (lower alkyl) phenyl, (hydroxy lower alkyl) phenyl, (lower alkanoyl) phenyl or quinolin-8-yl radical.

The thiosulfonate derivatives in question exert an inhibitory action with respect to the malformation or destruction of red blood corpuscules due to a genetic modification of haemoglobin or to parasites and can, therefore, be used in the treatment of drepanocytosis, malaria and babebiosis.

8 Claims, No Drawings

THIOSULFONATE DERIVATIVES FOR INHIBITING MALFORMATION OR DESTRUCTION OF RED BLOOD CORPUSCULES

This invention relates to novel thiosulfonate derivatives, to their process of preparation and to compositions containing them.

More particularly, the invention concerns the thiosulfonate derivatives of general formula:

$$R\text{—}S\text{—}SO_2\text{—}R_1 \qquad\qquad I$$

in which R represents a 1H-imidazol-2-yl, quinolin-2-yl, 5-amino-1,3,4-thiadiazol-2-yl or 4,5-dihydro-thiazol-2-yl radical and $R_1$ represents a lower alkyl, (hydroxy) lower alkyl, phenyl, (lower alkyl) phenyl, (hydroxy lower alkyl) phenyl, (lower alkanoyl) phenyl or quinolin-8-yl radical.

As used herein, the term "lower alkyl" means more particularly the methyl, ethyl, n-propyl and isopropyl groups and the term "lower alkanoyl" designates more particularly the formyl, acetyl and propionyl groups.

The compounds of formula I have been found to exert a very useful inhibitory action with respect to the malformation or destruction of red blood corpuscules due to a genetic modification of haemoglobin or to parasites.

Therefore, the invention also relates to pharmaceutical or veterinary compositions containing, as active principle, at least one thiosulfonate derivative of formula I, in association with a pharmaceutical carrier or excipient therefor.

Likewise, the invention relates to a method for inhibiting the malformation or destruction of red blood corpuscules due to a genetic modification of the haemoglobin or to parasites in a host in need of such inhibitory treatment whereby an effective dose of at least one thiosulfonate derivative of the invention is administered to the said host.

Another object of the invention concerns a process for preparing the compounds of formula I, whereby a mercapto derivative of general formula:

$$R\text{—}SH \qquad\qquad II$$

in which R has the same meaning as above, is reacted, in the presence of an acid acceptor, such as for example pyridine, with a halogenosulfonyl derivative of general formula:

$$Hal\text{—}SO_2\text{—}R_1 \qquad\qquad III$$

in which $R_1$ has the same meaning as above and Hal represents a halogen atom, preferably chlorine.

The reaction can be carried out in an appropriate organic solvent such as, for example, dichloromethane or acetonitrile.

It has been observed, however, that the molar ratio between the mercapto derivative of formula II and the halogenosulfonyl derivative of formula III is of paramount importance as is also the temperature, in regard to the yield in thiosulfonate derivative of formula I.

Thus, at room-temperature and following the molar ratio:

$$\frac{\text{compound of formula II}}{\text{compound of formula III}} = 2,$$

it is mainly the disulfides of formula R—S—S—R, in which R has the same meaning as above, which are obtained.

For instance, 90% of 2,2'-dithio-di-1H-benzimidazole is produced at room-temperature from 2-mercapto-1H-benzimidazole and benzenesulfonyl chloride in a 2:1 molar ratio.

However, by controling the temperature and modifying the molar ratio of the reagents of formulae II and III, it is principally the thiosulfonate derivatives of formula I which are produced.

In accordance with the invention, the process hereabove described is therefore carried out at a temperature from 0° to 10° C., generally at the temperature of iced water, the molar ratio $$\frac{\text{compound of formula II}}{\text{compound of formula III}}$$

varying from 1:1 to 1:4.

Generally a 1:2 molar ratio is preferred.

The compounds of formulae II and III above are known compounds and can be prepared by known methods.

Drepanocytosis is known to be a genetic disease involving an abnormality in the structure of the haemoglobin, whereby the Glu-6 amino acid of the β-chain is replaced by Val amino acid, giving haemoglobin-S which polymerizes.

This polymerization, during deoxygenation of the red cells, brings about sickling of the latter which become rigid, circulate poorly and are blocked in the small vessels. Individuals carrying two sickle cell genes are thus under the permanent threat of a fatal complication.

Certain disulfides have been described in the literature as inhibiting sickling, in particular cystamine, which has been found to be particularly active.('-'Developments of Therapeutic Agents for Sickle Cell Disease", Inserm Symposium, 1979, North Holland-:Amsterdam, Editors J. ROSA, Y. BEUZARD, J. HERCULES; p. 139–153).

On the other hand, no thiosulfonate derivative is known, at present, as presenting such an inhibitory action against sickling.

It has now been found that thiosulfonate derivatives i.e. the compounds of formula I above exert a marked inhibitory action against the polymerization of the haemoglobin-S and the sickling of the red cells.

It has also been unexpectedly found that the thiosulfonate derivatives of the invention are active against parasites affecting the red blood corpuscules, such as the Plasmodia and the Babesiae.

More particularly, the compounds of formula I have shown a schizonticide action in vitro on *Plasmodium falciparum* and in vivo on *Plasmodium berghei.*

The expression "inhibiting the malformation or destruction of red blood corpuscules" as used in the present context, means an inhibitory action which may be exerted either directly on the haemoglobin or indirectly by inhibition of the growth of parasites in the red cell.

In addition, the level of toxicity of compounds of the invention is not such as the hinder their therapeutic use.

Therefore, the compounds of the invention can be regarded as very valuable agents for inhibiting the malformation or destruction of red blood corpuscules due to a genetic modification of the haemoglobin or to parasites and therefore useful in the treatment of drepanocytosis, malaria and babebiosis.

Inhibition of the sickling of human red blood corpuscules was assessed by washing and incubating, in a saline buffer (pH: 7.40; 0.15M) for one hour at 37° C., the red cells of subjects suffering from drepanocytosis. This operation was carried out in a water-bath under stirring and in the presence of a compound of the invention used at different concentrations. The molar ratios between the compound of the invention and the haemoglobin were initially tested at intervals ranging from 0.5 to 20, the mM concentration in haemoglobin being 0.5 in each case and the ratio being modified according to the results obtained.

At the end of incubation, the excess of the product being tested was removed by washing and the cellular suspension adjusted so as to form a haematocrit of 5% was transferred to an Erlenmeyer flask and incubated at 37° C. under a current comprising a humidified mixture of nitrogen and oxygen the oxygen concentration being regulated by a gas-mixing pump. The effluent gas was then transferred to another tube containing formaldehyde and, at the end of incubation, the cellular suspension was transferred to the formaldehyde by merely turning the flask upside down.

The proportion of deformed cells and those having the characteristics of drepanocytes (having two filiform extensions) was assessed with the aid of a microscope having a NORMARSKY interferential optical system. Inhibition of sickling was calculated according to the following formula:

$$\frac{\% \text{ sickle-shaped cells used as controls} - \% \text{ sickle-shaped cells in the presence of the compound of the invention}}{\% \text{ sickle-shaped cells used as controls}}$$

The following results were obtained with representative compounds of the present invention in comparison with cystamine. These results represent the percentage of inhibition of sickling of the red blood corpuscules.

| Compound | Concentration (mmolar) | % inhibition |
| --- | --- | --- |
| 1H—Imidazol-2-yl p-toluene-thiosulfonate | 0.5 | 50 |
|  | 1 | 100 |
| 5-Amino-1,3,4-thiadiazol-2-yl p-toluenethiosulfonate | 1 | 33 |
| Cystamine | 5 | 33 |

These results show that the compounds of the invention inhibit sickling of the red blood corpuscules of patients suffering from drepanocytosis and are more active than the comparison compound.

It will be appreciated that, for therapeutic use, the compounds of the invention will normally be administered as active principle, in the form of a pharmaceutical or veterinary composition which may be in a dosage unit form appropriate to the desired mode of administration, for instance for oral sublingual, sub-cutaneous, intramuscular, intravenous, transdermic or rectal administration.

Thus, the composition may be in a dosage unit form suitable for oral administration for example a coated or uncoated tablet, a hard- or soft-gelatin capsule, a packaged powder, a suspension or a syrup for oral administration, a suppository for rectal administration, a sterile solution or suspension for parenteral administration.

When in dosage unit form, the composition may contain from 10 to 1000 mg of active principle per dosage unit form intended for oral, rectal or parenteral route.

Generally, one dosage unit will be required 1 to 4 times a day so that the daily dosage of active principle of the invention can vary from 0.1 to 100 mg per kg of body-weight for the treatment of drepanocytosis, malaria and babebiosis.

Irrespective of the form which they may take, the pharmaceutical or veterinary compositions of the invention will normally be prepared by associating at least one of the compounds of formula I with an appropriate pharmaceutical carrier or excipient, for example one or more of the following substances: distilled water, benzyl alcohol, lactose, starches, talc, magnesium stearate, polyvinylpyrrolidone, alginic acid, colloidal silica, microcrystalline cellulose, phthalic or acrylic esters, titanium dioxide, flavouring agents etc . . . .

A more detailed but non limitative description is given hereunder of various methods of preparing the compositions of the invention.

Powders for oral administration may be prepared, for example, by merely crushing the active principle to a suitably fine consistency and mixing it with a diluent similarly treated which may be, for instance, an edible glucide derivative such as starch.

Preferably, a sweetening agent or a sugar together with a flavouring oil will be included.

To obtain a liquid composition for oral administration, granules are prepared by wetting the active principle of the invention and a water-soluble diluent such as saccharose, glucose etc . . . , with a binding agent such as acacia mucilage, gelatin solution or methylcellulose solution and forcing the resulting product through a screen to form granules which are then dried.

Preferably, the composition will contain a suspension agent such as gum tragacanth.

Similarly, a composition of the invention in the form of a capsule may be obtained by introducing a pulverulent mixture as described above into previously prepared soft- or hard-gelatin shells.

As an aid to the filling operation, it will be advantageous to add a lubricant such as talc, magnesium stearate or calcium stearate to the pulverulent mixture.

Tablets can also be obtained by first preparing a pulverulent mixture from an active compound of the invention suitably crushed and a diluent or a base such as starch, saccharose, kaolin, dicalcium phosphate etc . . . . This pulverulent mixture is then granulated or cut up after a lubricant has been added and is finally compressed.

The pulverulent mixture may be granulated by wetting with a binding agent such as syrup, starch paste or acacia mucilage and forcing it through a screen.

Another method of granulation consists in dividing up the pulverulent mixture, by passing it through a tablet-making apparatus and then fragmenting the imperfectly formed tablets obtained. The fragments may be lubricated by adding a stearate salt, talc or mineral oil to prevent them from forming cubes by sticking to each other.

The lubricated mixture is then compressed to form the final tablets.

The tablets may be covered with a protective coating or an enteric-coating or again coated so that the active principle is gradually released.

A composition of the invention for rectal administration can also be prepared in the form of a suppository by pouring, into an appropriate mould, a mixture formed of the active principle of the invention and a binding agent melting at rectal temperature, for instance cocoa butter, polyethyleneglycols or lanoline.

For parenteral administration, aqueous suspensions, isotonic saline solutions or sterile and injectable solutions can be prepared comprising an active compound of the invention together with a solubilizing agent, if required, for example polysorbate 80, appropriate wetting agents for instance propyleneglycol or butyleneglycol and a preserving agent such benzyl alcohol.

The active principle can also be presented in the form of microcapsules optionally with one or more additives.

The non-limitative Examples which follow illustrate the invention:

EXAMPLE 1

Preparation of 1H-imidazol-2-yl p-toluenethiosulfonate

In a 500 ml three-necked flask fitted with a condenser and a magnetic stirrer were dissolved, under adequate stirring, 3.81 g (0.02 mol) of p-toluenesulfonyl chloride in 40 ml of dichloromethane. To the solution so formed there were added 3.16 g (0.04 mol) of pyridine previously dried on magnesium sulfate.

The flask was placed in a bath of iced water at 4° C. and while the reaction medium was maintained under stirring at a temperature of the iced water there was slowly added (addition period: >3 hours) drop-by-drop 1 g (0.01 mol) of 2-mercapto-1H-imidazole dissolved in 160 ml of dichloromethane.

The reaction medium was kept under vigorous stirring for 24 hours at 4° C. A cream-coloured precipitate progressively appeared in the flask. To facilitate the formation and recovery of the solid, a part of the solvent was evaporated off under vacuum be very gentle heating (about 50° C.). The precipitate was collected by filtration on fritted glass and dried. The product was then washed 3 times with ethanol and recrystallised from the same solvent.

In this manner, 1H-imidazol-2-yl p-toluenethiosulfonate was obtained.

Yield: 35%

Empirical formula: $C_{10}H_{10}N_2O_2S_2$

|  | Analysis: | | | | |
|---|---|---|---|---|---|
|  | C % | H % | N % | O % | S % |
| Calculated | 47.23 | 3.96 | 11.01 | 12.58 | 25.21 |
| Found | 47.02 | 4.18 | 10.85 | 12.96 | 24.49 |

M.P.: 87° C.

Following the same procedure as that described above, the following compounds were obtained:

(a) From 8-quinolinsulfonyl chloride and 2-mercapto-quinolin, quinolin-2-yl 8-quinolinthiosulfonate Yield: 60%

Empirical formula: $C_{18}H_{12}N_2O_2S_2$

|  | Analysis: | | | | |
|---|---|---|---|---|---|
|  | C % | H % | N % | O % | S % |
| Calculated | 61.35 | 3.43 | 7.95 | 9.08 | 18.20 |
| Found | 62.06 | 3.57 | 8.10 | 8.17 | 18.20 |

M.P.: 144° C.

(b) From p-toluenesulfonyl chloride and 2-mercapto-5-amino-1,3,4-thiadiazol, 5-amino-1,3,4-thiadiazol-2-yl p-toluenethiosulfonate.

Yield: 30%

Empirical formula: $C_9H_9N_3O_2S_3$

|  | Analysis: | | | | |
|---|---|---|---|---|---|
|  | C % | H % | N % | O % | S % |
| Calculated | 37.62 | 3.16 | 14.62 | 11.13 | 33.47 |
| Found | 37.92 | 3.10 | 14.29 | 12.01 | 32.63 |

M.P.: 194° C.

(c) From methanesulfonyl chloride and 2-mercapto-4,5-dihydro-thiazole, 4,5-dihydro-thiazol-2-yl methanethiosulfonate (reaction solvent: acetonitrile)

Yield: 25%

Empirical formula: $C_4H_7NO_2S_3$

|  | Analysis: | | | | |
|---|---|---|---|---|---|
|  | C % | H % | N % | O % | S % |
| Calculated | 24.35 | 3.58 | 7.10 | 16.22 | 48.75 |
| Found | 24.50 | 3.63 | 7.71 | 15.35 | 47.55 |

M.P.: 162° C.

(d) From benzenesulfonyl chloride and 2-mercapto-4,5-dihydro-thiazole, 4,5-dihydro-thiazol-2-yl benzenethiosulfonate (reaction solvent: acetonitrile)

Yield: 40%

Empirical formula: $C_9H_9NO_2S_3$

|  | Analysis: | | | | |
|---|---|---|---|---|---|
|  | C % | H % | N % | O % | S % |
| Calculated | 41.68 | 3.50 | 5.40 | 12.34 | 37.09 |
| Found | 40.11 | 3.86 | 5.53 | 11.82 | 36.49 |

M.P.: 158° C.

EXAMPLE 2

Tablets were prepared containing, as active ingredient, a thiosulfonate derivative of the invention, associated with a carrier to form the composition given hereunder:

|  | mg |
|---|---|
| Compound of the invention | 500 |
| Glycine | 120 |
| Microcrystalline cellulose | 70 |
| Precipitated silica | 18 |
| Carboxymethylstarch | 30 |
| Magnesium stearate | 11 |
| Talc | 11 |

The ingredients of the above composition were mixed for 30 minutes and the resulting mixture was granulated dry and passed through a sieve with 1.6 mm mesh. The mixture was then compressed using a punch in the form of a small rod. Tablets were thus obtained each weighing 760 mg and each containing 500 mg of active ingredient.

EXAMPLE 3

Coated tablets were prepared by coating the tablets obtained in Example 2 with a suspension of dibutyl phthalate, butyl and dimethylaminoethyl polymethacrylate, polyethyleneglycol 1500, precipitated silica, titanium dioxide and talc in a 1:1 acetone/isopropanol mixture having a concentration of dry residue of about 10%.

In this manner, coated tablets were obtained each weighing 780 mg and each containing 500 mg of active ingredient.

EXAMPLE 4

Granules intended for the reconstitution of a liquid preparation for oral administration was prepared containing, as active ingredient, a thiosulfonate derivative according to the invention, associated with a carrier to form the following composition:

|  | g |
|---|---|
| Compound of the invention | 3.60 |
| Saccharose | 50.00 |
| Sodium carboxymethylcellulose | 0.80 |
| Citric acid | 0.10 |
| Trisodium citrate | 0.90 |
| Sodium benzoate | 0.25 |
| Sodium saccharine | 0.15 |
| Flavouring agent | 0.50 |

The above ingredients, with the exception of saccharose, were pulverized and the powder so obtained was mixed with the saccharose until homogeneous granules were obtained.

The volume of the granules so provided was increased to 100 ml with water intended for the preparation of syrups.

A unit dose of 5 ml of the extemporaneous syrup thus obtained contained 180 mg of active principle.

EXAMPLE 5

Granules intended for the reconstitution of an oral liquid preparation having the composition given below were prepared as described in Example 4:

|  | g |
|---|---|
| Compound of the invention | 7.00 |
| Saccharose | 46.60 |
| Sodium carboxymethylcellulose | 0.90 |
| Citric acid | 0.10 |
| Trisodium citrate | 0.90 |
| Sodium benzoate | 0.25 |
| Sodium saccharine | 0.15 |
| Flavouring agent | 0.50 |

An unit dose of 5 ml of extemporaneous syrup was obtained containing 350 mg of active principle.

EXAMPLE 6

Granules intended for the reconstitution of an oral liquid preparation, having the following composition, were prepared as described in Example 4:

|  | g |
|---|---|
| Compound of the invention | 8.00 |
| Saccharose | 45.60 |
| Sodium carboxymethylcellulose | 1.00 |
| Citric acid | 0.10 |
| Trisodium citrate | 0.90 |
| Sodium benzoate | 0.25 |
| Sodium saccharine | 0.15 |
| Flavouring agent | 0.50 |

An unit dose of 5 ml of extemporaneous syrup was obtained containing 400 mg of active principle.

EXAMPLE 7

Tablets having the following composition were prepared containing a compound described in Example 1:

|  | mg |
|---|---|
| Compound of the invention | 350 |
| Microcrystalline cellulose | 100 |
| Lactose | 125 |
| Magnesium stearate | 10 |
| Talc | 15 |
|  | 600 |

The powder was passed through a sieve with 0.3 mm mesh and the ingredients were mixed together until a homogeneous mixture was obtained which was compressed and granulated.

The granules thus obtained were compressed into tablets.

EXAMPLE 8

Tablets containing a compound described in Example 1 were prepared having the following composition:

|  | mg |
|---|---|
| Compound of the invention | 150 |
| Microcrystalline cellulose | 75 |
| Talc | 15 |
| Polyvinylpyrrolidone | 30 |
| Precipitated silica | 25 |
| Magnesium stearate | 5 |
|  | 300 |

All the ingredients with the exception of the lubricant, were thoroughly mixed in a mixing-kneading apparatus for 15 min. and the mixture obtained was kneaded with the gradual addition of water. The mass was passed through a sieve of 1.25 mm mesh and the granules were dried in an oven with forced ventilation until a relatively low degree of residual humidity (about 2%) was obtained. The granules were rendered uniform, the lubricant was added and the tablets were formed by compression.

Following the procedure described above, tablets containing 250 mg of active principle of the invention were prepared.

EXAMPLE 9

Coated tablets containing a compound described in Example 1 were prepared having the following composition and operating as described in Example 8:

|  | mg |
|---|---|
| Compound of the invention | 150 |
| Carboxymethylstarch | 10 |
| Microcrystalline cellulose | 85 |
| Lactose | 135 |
| Hydrogenated castor oil | 10 |
| Magnesium stearate | 5 |

The tablets thus obtained were covered with a coat having the following composition:

|  | mg |
| --- | --- |
| Butyl phthalate | 0.300 |
| Butyl and dimethylaminoethyl polymethacrylate | 1.850 |
| Polyethyleneglycol 1500 | 0.080 |
| Precipitated silica | 0.020 |
| Talc | 0.900 |
| Titanium dioxide | 1.850 |

This composition was dissolved in a solvent which was evaporated off in an oven with forced ventilation. Weigh of a tablet: 400 mg.

EXAMPLE 10

Suppositories having the following composition were prepared containing a compound described in Example 1:

|  | mg |
| --- | --- |
| Compound of the invention | 300 |
| Mass for suppositories | 1 450 |
|  | 1 750 |

The finely pulverized active substance was suspended in the mass for suppositories at 37° C. and the mixture was poured into moulds which were slightly cooled beforehand.

We claim:

1. A thiosulfonate derivative having a formula:

$$R-S-SO_2-R_1$$

in which R represents a 1H-imidazol-2-yl radical and $R_1$ represents a lower alkyl, (hydroxy) lower alkyl, phenyl, (lower alkyl) phenyl, (hydroxy lower alkyl) phenyl, (lower alkanoyl) phenyl or quinolin-8-yl radical.

2. 1H-imidazol-2-yl p-toluenethiosulfonate.

3. A pharmaceutical or veterinary composition containing, as active ingredient, an effective amount for inhibiting the malformation or destruction of red blood corpuscles due to a genetic modification of haemoglobin or to parasites, of at least one thiosulfonate derivative according to claim 1 in association with a pharmaceutical carrier or excipient therefor.

4. A pharmaceutical or veterinary composition containing, as active ingredient, an effective amount for inhibiting the malformation or destruction of red blood corpuscles due to a genetic modification of haemoglobin or to parasites, of at least one thiosulfonate derivative according to claim 2 in association with a pharmaceutical carrier or excipient therefor.

5. A composition according to claim 3 in the form of a dosage unit.

6. A composition according to claim 5 whereby each dosage unit contains from 10 to 1000 mg of active ingredient.

7. Method for inhibiting the malformation or destruction of the red blood corpuscules due to a genetic modification of the haemoglobin or to parasites in a host in need of such inhibitory treatment comprising the administration to the said host of an effective dose of at least one thiosulfonate derivative according to claim 1.

8. Method according to claim 7 whereby the effective dose is 0.1 to 100 mg/kg body-weight.

* * * * *